United States Patent [19]

Kachel et al.

[11] 4,253,058
[45] Feb. 24, 1981

[54] DEVICE FOR MEASURING CERTAIN PROPERTIES OF PARTICLES SUSPENDED IN A PARTICLE SUSPENSION

[75] Inventors: Volker Kachel, Puchheim; Ewald Glossner, Nandlstadt, both of Fed. Rep. of Germany

[73] Assignee: Max-Planck-Gesellschaft zur Foerderung der Wissenschaften e.V., Goettingen, Fed. Rep. of Germany

[21] Appl. No.: 960,272

[22] Filed: Nov. 13, 1978

[30] Foreign Application Priority Data

Nov. 11, 1977 [DE] Fed. Rep. of Germany ....... 2750447

[51] Int. Cl.³ .................... G01N 15/07; G01N 27/07
[52] U.S. Cl. .............................................. 324/71 CP
[58] Field of Search ................ 324/71 CP; 73/432 PS

[56] References Cited

U.S. PATENT DOCUMENTS

| Re. 28,558 | 9/1975 | Hogg | 324/71 CP |
|---|---|---|---|
| 3,299,354 | 1/1967 | Hogg | 324/71 CP |
| 3,793,587 | 2/1974 | Thomet et al. | 324/71 CP |
| 4,014,611 | 3/1977 | Simpson et al. | 324/71 CP X |
| 4,140,966 | 2/1979 | Godin et al. | 324/71 CP |
| 4,157,498 | 6/1979 | Johnson | 324/71 CP |
| 4,165,484 | 8/1979 | Haynes | 324/71 CP |

FOREIGN PATENT DOCUMENTS 2462063 11/1975 Fed. Rep. of Germany ...... 324/71 CP

Primary Examiner—Gerard R. Strecker
Attorney, Agent, or Firm—Edwin E. Greigg

[57] ABSTRACT

In a so-called Coulter-device with a first and a second chamber, a separating wall between them and a measuring aperture in the separating wall, through which particle-free electrolyte flows from the first chamber into the second chamber, and with first and second electrodes in the first and second chamber resp., at which a measuring impulse indicating a certain property (e.g. volume) is derived upon the passage of a particle, which is supplied to it through a supply capillary ending in front of the measuring aperture, the improvement consisting in means to supply additional particle-free electrolyte to the particle stream at and/or in the neighborhood of the downstream end of the measuring aperture to deflect those particles, which, after passage through the measuring aperture, travel backward to the same and cause error impulses.

3 Claims, 6 Drawing Figures

DEVICE FOR MEASURING CERTAIN PROPERTIES OF PARTICLES SUSPENDED IN A PARTICLE SUSPENSION

BACKGROUND OF THE INVENTION

The invention is concerned with a device for measuring certain properties of particles suspended in a particle suspension with a first chamber, to which particle-free electrolyte is supplied, a separating wall and a second chamber, which is connected with the first chamber by means of a measuring aperture in the separating wall, with a pressure in the second chamber, which for generating the flow of a stream of particle-free electrolyte through the measuring aperture is less than the pressure in the first chamber, and a particle supply capillary in the first chamber in front of the measuring aperture, out of which the particle containing particle suspension is introduced into said stream, to transport the particles through the measuring aperture such that upon passage of a particle through the measuring aperture a measuring impulse is obtained between a first and a second electrode, which are provided in the first and in the second chamber respectively (U.S. Pat. No. 2,656,508).

With these devices the problem exists that some of the particles, which have passed the measuring aperture and have entered the second chamber, separate from the main flow of the stream of electrolyte. Such separation can be effected for example by the formation of vortices or turbulence. These particles then can return to the downstream side of the measuring aperture. If they reenter the area around the downstream end of the measuring aperture, in which already a concentration of the electrical field lines is present, they can induce impulses between the electrodes. These impulses are smaller than those, which the same particles would effect when passing through the measuring aperture. However, they are large enough to be included in an evaluation of the impulses, e.g. by classification in accordance to their height, since e.g. an impulse induced by a backwards travelling erythrocyte can have approximately the same height as the one induced by a thrombocyte upon passage of the measuring aperture. This means that the evaluation of the impulses is erroneous, when impulses as generated by backward travelling particles are evaluated as actually measuring impulses as generated by normal passage of particles through the measuring aperture.

For solving this problem of the backward travelling particles it has been suggested (U.S. Pat. No. 3,299,354, col. 2, lines 24–30) to provide downstream behind the measuring aperture a suction capillary, the entrance of which serves as a secondary aperture, through which the particle stream entering the second chamber is sucked in order to completely separate the particles from the second chamber shortly after they have entered it and thereby avoid the occurrence of particles travelling back to the measuring aperture. Within this suction capillary by suitable geometrical construction it is provided that these backward travelling particles are collected at a certain point such that they cannot again travel back through the secondary aperture (see op. cit., reference a numeral 44, col. 5, line 20). It is a disadvantage of this arrangement that special provisions are necessary to clean the suction capillary, in which the secondary aperture is provided (op. cit., col. 5, line 69 ) to col. 6, line 8). Also, this device is of an intricate and complicated construction.

Further devices are known, with which for each particle two measuring impulses are generated in a certain timely sequence upon passage through two apertures (DT-OS No. 21 11 356). With these devices, in the space between both measuring apertures, particle-free electrolyte is supplied. However, once a particle has passed the second measuring aperture, the backward travelling particles problem still exists in the same manner. No solution of this problem has been suggested.

It is the objective of the present invention to improve the device as aforementioned, in which the backward travelling particles problem, as explained, shall be avoided. In particular, the particles, which have entered the second chamber, shall be prevented from reaching the neighbourhood of the downstream end of the measuring aperture. This objective shall be accomplished without the necessity of providing behind the aperture a suction capillary with a secondary aperture, since this is considered to be constructively too complicated and difficult to clean.

In accordance the invention a device as aforementioned has the following improvements:

That in the direction of stream flow downstream behind the end of the measuring aperture means are provided for additional supplying particle-free electrolyte to combine with said flowstream to surround the same and deflect particles, which, in the second chamber, travel backward to the downstream end of the measuring aperture.

By providing additional outlets of particle-free electrolyte, preferably from radially extending channels, at a position downstream after the mesuring aperture, an additional flow of electrolyte is provided, which surrounds the particle stream at this position, whereby this additional electrolyte flow keeps away the backward travelling particles from the measuring aperture. This additional flow or stream serves as a sort of screening of the downstream end of the measuring aperture. This solution is extremely simple and obviates the necessity of providing special suction means to transport and separate the particle stream. It further has the advantage that the same means can be used to clean the measuring aperture by rinsing or flushing in those cases, in which particles stick to the same. Such flushing effect, to some extend, is achieved simultaneously with screening the measuring aperture. Further improvement will become apparent from the description.

An embodiment of the invention is described in the following with reference to the accompanying drawings. In the drawings:

DESCRIPTION OF THE PREFERRED EMBODIMENT

Figure 1:
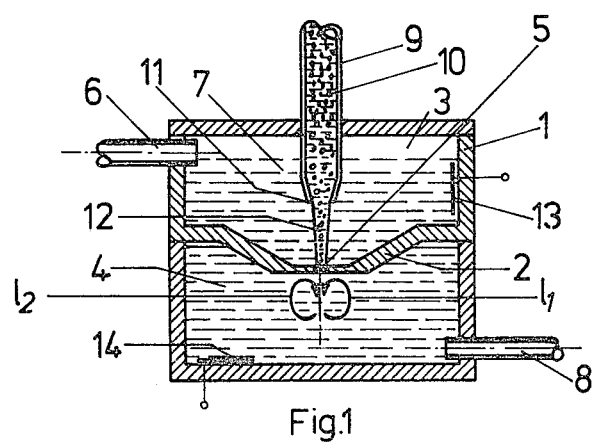
FIG. 1 is a schematic illustration of a known device.

FIG. 1 shows schematically the construction of a known measuring device of the type to be improved by the invention. A housing 1 is separated by a separating wall 2 in a first chamber 3 and a second chamber 4. A measuring opening or aperture 5 is provided in the separating wall 2. From a supply line 6 particle-free electrolyte 7 is supplied to the chamber 3. By connecting a negative pressure source (not shown) to the tube 8 a pressure is generated in the second chamber 4, which is lower than the one in the first chamber 3. By this pressure difference between the first chamber 3 and the second chamber 4 particle-free electrolyte is sucked from chamber 3 through measuring aperture 5 into the second chamber 4. Above or in front of the measuring aperture 5 there is provided a supply capillary 9, which serves to supply a particle suspension 10 to the measuring device. Within this suspension the particles, the properties of which (e.g. their volume) shall be measured, are held in suspension. The pressure of the particle suspension at the outlet opening 11 of the particle supply capillary 9 is higher than the pressure in the first chamber 3. As a consequence, particle suspension emerges from the outlet opening 11 into the first chamber 3. This particle stream is focussed on its path to the measuring aperture 5 as a consequence of the fact that the flow of particle-free electrolyte is narrowed and converges in the direction of the measuring aperture 5. Within the first chamber 3, a first electrode 13 and within the second chamber 4 a second electrode 15 are provided, which are connected to appropriate terminals. By appropriate current supply means (not shown) a constant current is supply to pass between electrodes 13, 14. The electrical properties of the particles differ from the electrolyte. Therefore, when a particle passes through the measuring aperture 5, the electrical field lines in the measuring aperture 5 are displaced, and therefore the resistance of the electrical electrodes 13, 14 also will change. If the current is kept constant, this change in restistance results in a change of voltage between electrodes 13, 14. This provides an impulse, the height of which is proportional to the volume of the particle. As so far described, these devices are known (U.S. Pat. No. 2,656,508).

Figure 2:
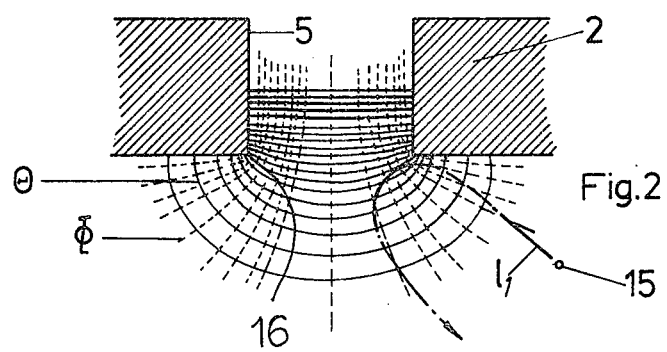
FIG. 2 shows the electrical field in the measuring aperture of the device described in FIG. 1.
Figure 3:
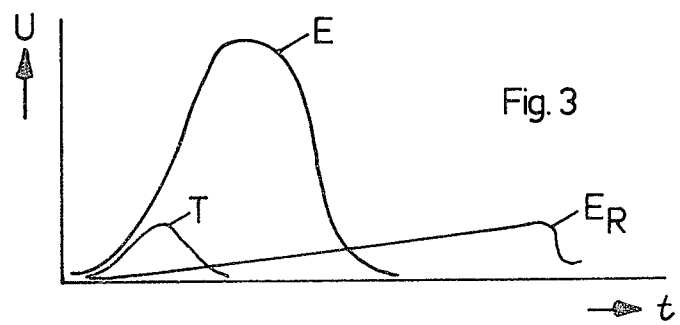
FIG. 3 shows certain different impulses, which are obtained upon the passage of particles through the measuring aperture in the device in accordance to FIG. 1.

Referring to the problem of backward travelling particles, the following occurs: As can be seen from FIG. 2, particles 15, which already have passed the measuring aperture, are not all at once and with certainty led away through tube 8. It is rather possible that individual particles, as indicated by lines $l_1$ and $l_2$, are engaged in some type of turbulence or vortex forming action after the downstream end 16 of the measuring aperture 5. This turbulence possibly can bring them back in the neighbourhood of the downstream end 16 of the measuring aperture 5. Such a situation is depicted in FIG. 2 on an enlarged scale. The lines of equipotential are referred to by $\phi$, the field lines are depicted by $\phi$. If a particle 15 passes along path $l_1$ through the area of increased concentration of the fieldlines in the neighbourhood of the downstream end 16 of measuring aperture 5, a backward travelling particle impulse is generated. This is shown in FIG. 3. E is a normal measuring impulse, which occurs, if e.g. an erythrocyte passes through the measuring apertures 5; T is a measuring impulse, which occurs upon the passage of a thrombocyte through the measuring aperture 5. $E_R$ is a backward travelling particle impulse as it occurs, if 5 is an erythrocyte, and it moves back to the measuring aperture along path $l_1$. If the measuring impulses are classified in accordance to their height, it is possible that a backward travelling particle impulse $E_R$ is erroneously evaluated as an impulse stemming from a thrombocyte T, which is of approximately the same height. The construction of the device in accordance to an embodiment of the invention as depicted in FIG. 4 and 6 avoids these errors, as will be explained in the following.

Figure 4:
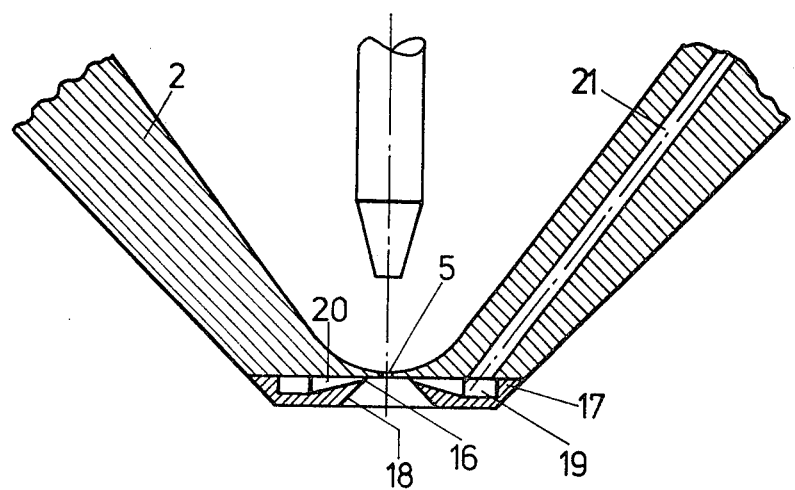
FIG. 4 is a cross-section through the separating wall 2 of a device in accordance to an embodiment of the invention.

In FIG. 4 the separating wall 2 also has a measuring aperture 5. Next to the downstream end 16 of the measuring aperture 5 a ring 17 is provided in close relation and attached thereto, which has a conical passage 18, which expands in downstream direction. In the upper side of the ring 17, an anular channel 19 is provided, which is connected with the passage 18 by means of 6 radial channels 20. Further, the anular channel 19 is in connection with a supply line 21, which also is provided within the separating wall 2. By means of the supply line 21 particle-free electrolyte is supplied to the anular channel 19. Through the radial channels 20 the electrolyte passes into the passage 18 and thereby into the chamber 4. In particular it enters chamber 4 right after the downstream end 16 of the measuring aperture 5. The stream of particle-free electrolyte emerging from radial channels 20, which has a pressure slightly above the one of the particle suspension in the chamber 4, surrounds the particle stream 12. It therefore acts as a type of "screening" or "shielding", which provides that backward travelling particles 15, 15' cannot come in such a close distance to the measuring opening 5 that backward travelling particle impulses, e.g. $E_R$, can be generated.

Figure 6:
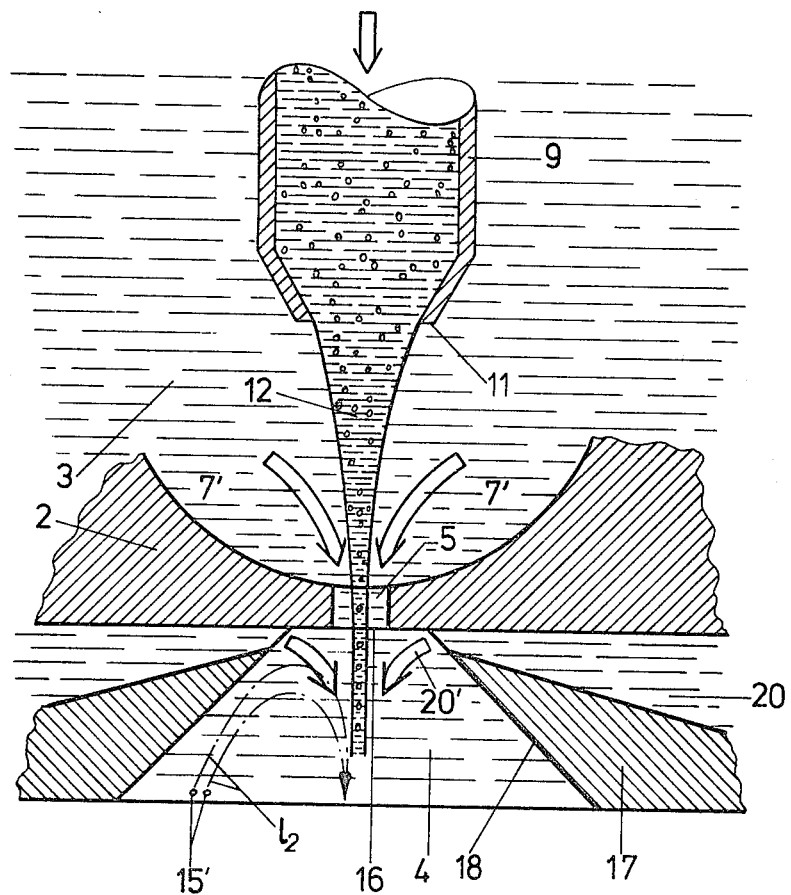
FIG. 6 is a further illustration for purposes of explaining the embodiment of the invention in accordance to FIG. 4.

This situation is again demonstrated on a larger scale in FIG. 6. First, as per se known, the particle stream 12 is focussed by the conditions of flow of the particle-free electrolyte before and on to the measuring aperture 5. The flow of the particle-free electrolyte on to the measuring aperture is indicated by arrows 7'. Downstream behind the measuring aperture 5 this particle stream 12 is surrounded by the flow of particle-free electrolyte, which emerges from channels 20 as it is indicated by arrows 20'. This flow 20' deflects particles 15', which travel on a path $l_2$ backward to the downstream end 16 of the measuring aperture 5. Now and therefore they can no longer reach the end 16 of the measuring aperture 5 and generate a registerable impulse. The flow 20' from the radially arranged channels 20 in this manner prevents the backward travelling particles from reaching that region.

At the same time the flow 20' has continuously a rinsing or cleaning effect at the end 16 of measuring aperture 5. This cleaning or rinsing action serves to prevent that particles, which separate from the particle-stream 12, can be deposited or stick to the surface of the measuring aperture 5 around its end 16. This rinsing or cleaning effect, naturally, can also be made use of in the absence of a particle stream 12 to effect cleaning of the measuring aperture.

Figure 5:
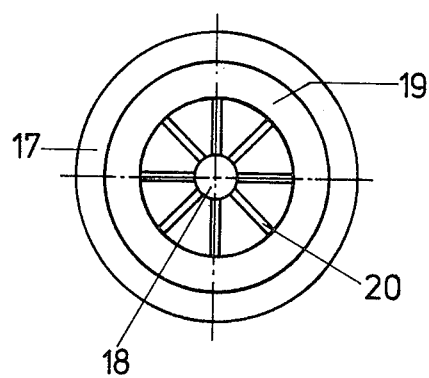
FIG. 5 is a section along the line V—V in FIG. 4.

In summary, one is well aware with "Coulter" devices for which there are already a various number of applications. As one can best see from FIGS. 4 and 6, once the particle containing suspension flow has passed through the measuring aperture 5, backwards traveling particles (see e.g. 15 in FIG. 2), caused by vortices or other disturbances, may again come within the range at the end 16 of the aperture 5, in which the field lines are still concentrated and give rise to error pulses. To prevent this, the invention provides downstream behind the separating wall a ring 17 with a plurality of radially extending channels 20 (see FIG. 5), through which a particle-free electrolyte is introduced (see arrows 20' in FIG. 6), to keep the downstream end of the measuring aperture clean and provide a separation flow to divert particles, which might have been traveling backwards, from reaching the end of the aperture (See path 15' in FIG. 6).

What is claimed is:

1. Device for measuring certain properties of particles suspended in a particle suspension comprising
   a first chamber to which a particle-free electrolyte is supplied,
   a second chamber,
   a separating wall between said first chamber and said second chamber,
   a particle supply capillary in the first chamber in front of the measuring aperture,
   a measuring aperture in the separating wall,
   pressure generating means for providing a pressure in the second chamber which is less than the pressure in the first chamber to generate a flow of particle-free electrolyte through the measuring aperture from the first chamber into the second chamber, into which flow the particle containing suspension is introduced from the particle supply capillary,
   means proximate to said separating wall providing a conically widening passage 18 at the downstream end of the measuring aperture opening into said second chamber,
   a plurality of channels 20, adapted to be supplied with additional particle-free electrolyte, positioned within the walls of said conically widening passage 18 opening into said conically widening passage in a radial direction with respect to the axis of the flow through the measuring aperture for introducing said additional particle-free electrolyte into said passage to surround the particle stream flowing through said aperture and deflect any particles flowing backward toward the downstream end of the measuring aperture.

2. Device in accordance to claim 1, characterized in that a plurality of radially extending channels are provided, to which particle-free electrolyte is fed through an anular chamber, which is connected to a supply line.

3. Device in accordance to claim 1, characterized in that the channels are provided in the vicinity of and to extend in the direction on to the measuring aperture that, upon supply of cleaning liquid to it, it flushes the downstream end of the measuring aperture.

* * * * *